United States Patent
Van Dam et al.

(10) Patent No.: US 11,584,721 B2
(45) Date of Patent: *Feb. 21, 2023

(54) PROCESS FOR MANUFACTURING A MIXTURE OF STRAIGHT-HAIN AND NON-STRAIGHT-CHAIN ETHYLENEAMINES

(71) Applicant: NOURYON CHEMICALS INTERNATIONAL B.V., Arnhem (NL)

(72) Inventors: Hendrik Van Dam, Ede (NL); Karl Fredrik Lake, Södertälje (SE); Eike Nicolas Kantzer, Uddevalla (SE); Antoon Jacob Berend Ten Kate, Arnhem (NL); Rolf Krister Edvinsson, Partille (SE); Michiel Jozef Thomas Raaijmakers, Deventer (NL); Rens Veneman, Amersfoort (NL); Ina Ehlers, Stenungsund (SE); Jenny Valborg Therese Adrian Meredith, Årsta (SE); Slavisa Jovic, Utrecht (NL)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/630,287

(22) PCT Filed: Jul. 3, 2018

(86) PCT No.: PCT/EP2018/067867
§ 371 (c)(1),
(2) Date: Jan. 10, 2020

(87) PCT Pub. No.: WO2019/011709
PCT Pub. Date: Jan. 17, 2019

(65) Prior Publication Data
US 2020/0361873 A1    Nov. 19, 2020

(30) Foreign Application Priority Data
Jul. 10, 2017 (EP) ..................................... 17180569

(51) Int. Cl.
*C07D 233/02* (2006.01)
*C07C 209/70* (2006.01)
*C07C 209/16* (2006.01)

(52) U.S. Cl.
CPC .......... *C07D 233/02* (2013.01); *C07C 209/16* (2013.01); *C07C 209/70* (2013.01)

(58) Field of Classification Search
None
See application file for complete search history.

(56) References Cited

U.S. PATENT DOCUMENTS

| | | | |
|---|---|---|---|
| 2,812,333 A | 11/1957 | Steele | |
| 3,133,932 A | 5/1964 | Horn et al. | |
| 4,387,249 A | 6/1983 | Harnden et al. | |
| 4,503,250 A | 3/1985 | Herdle | |
| 4,568,745 A | 2/1986 | Ghelli et al. | |
| 4,684,729 A | 8/1987 | Duquette et al. | |
| 5,262,534 A | 11/1993 | King | |
| 5,364,971 A | 11/1994 | Su | |
| 5,491,263 A | 2/1996 | Rooney et al. | |
| 10,995,077 B2 * | 5/2021 | Edvinsson | C07D 295/13 |

(Continued)

FOREIGN PATENT DOCUMENTS

| | | |
|---|---|---|
| CN | 103987757 A | 8/2014 |
| EP | 0222934 A1 | 5/1987 |

(Continued)

OTHER PUBLICATIONS

Ahlers ("Triethylenetetramine" Screening Information Data Set of the Organization for Economic Co-Operation and Development (OECD SIDS), published by UNEP Publications, Jul. 1998, p. 1-63) (Year: 1998).*
Santa Cruz Biotechnology MSDS sheet for TEPA, downloaded from https://datasheets.scbt.com/sc-237036.pdf on Dec. 4, 2020, p. 1-14 (Year: 2020).*
Wikipedia entry for TEPA, downloaded from https://en.wikipedia.org/wiki/Tetraethylenepentamine#:~:text=Tetraethylenepentamine%20(TEPA)%20is%20an%20organic,soluble%20in%20most%20polar%20solvents on Dec. 4, 2020 (Year: 2020).*
Dow ("Ethyleneamines", published Oct. 2009, p. 1-46) (Year: 2009).*
ISA, European Patent Office, International Search Report and Written Opinion issued in International Application No. PCT/EP2018/067866, dated Sep. 14, 2018.

(Continued)

*Primary Examiner* — Amy C Bonaparte
(74) *Attorney, Agent, or Firm* — Lorenz & Kopf, LLP

(57) ABSTRACT

A process for manufacturing a mixture of straight-chain higher ethyleneamines and non-straight-chain higher ethyleneamines selected from branched higher ethyleneamines and cyclic higher ethyleneamines, or the urea derivatives thereof, includes reacting an amine-functional compound with an ethanolamine-functional compound in the presence of a carbon oxide delivering agent, wherein a) an amine-functional compound comprises a combination of straight-chain amine-functional compound and non-straight-chain amine-functional compound and is reacted with straight-chain ethanolamine-functional compound, or b) a straight-chain amine-functional compound is reacted with ethanolamine-functional compound comprising a combination of straight-chain ethanolamine-functional compound and non-straight-chain ethanolamine-functional compound, or c) an amine-functional compound comprising a combination of straight-chain amine-functional compound and non-straight-chain amine-functional compound is reacted with ethanolamine-functional compound comprising a combination of straight-chain ethanolamine-functional compound and non-straight-chain ethanolamine-functional compound.

17 Claims, No Drawings

(56) References Cited

U.S. PATENT DOCUMENTS

| | | | |
|---|---|---|---|
| 2007/0100144 A1 | 5/2007 | Frauenkron et al. | |
| 2010/0029976 A1 | 2/2010 | Dahmen et al. | |
| 2010/0087681 A1 | 4/2010 | Petraitis et al. | |
| 2010/0087683 A1 | 4/2010 | Cook et al. | |
| 2010/0120983 A1 | 5/2010 | Dufaure et al. | |
| 2019/0031597 A1* | 1/2019 | Edvinsson | C07C 273/1809 |
| 2019/0047971 A1* | 2/2019 | Edvinsson | C07D 295/13 |

FOREIGN PATENT DOCUMENTS

| | | | |
|---|---|---|---|
| EP | 1654214 B1 | 3/2007 | |
| EP | 2548869 A1 | 1/2013 | |
| FR | 2912148 | 8/2008 | |
| GB | 1510538 | 5/1978 | |
| WO | WO-2017137530 A1 * | 8/2017 | C07D 295/13 |

OTHER PUBLICATIONS

ISA, European Patent Office, International Search Report and Written Opinion issued in International Application No. PCT/EP2018/067867, dated Aug. 20, 2018.

ISA, European Patent Office, International Search Report and Written Opinion issued in International Application No. PCT/EP2018/067868, dated Oct. 1, 2018.

ISA, European Patent Office, International Search Report and Written Opinion issued in International Application No. PCT/EP2018/067869, dated Sep. 14, 2018.

EPO, European Extended Search Report issued in European Patent Application No. 17180568.2, dated Oct. 13, 2017.

EPO, European Extended Search Report issued in European Patent Application No. 17180569.0, dated Jan. 22, 2018.

EPO, European Extended Search Report issued in European Patent Application No. 17180571.6, dated Jan. 22, 2018.

EPO, European Extended Search Report issued in European Patent Application No. 17180573.2, dated Jan. 22, 2018.

* cited by examiner

PROCESS FOR MANUFACTURING A MIXTURE OF STRAIGHT-HAIN AND NON-STRAIGHT-CHAIN ETHYLENEAMINES

CROSS-REFERENCE TO RELATED APPLICATION

This application is a U.S. National-Stage entry under 35 U.S.C. § 371 based on International Application No. PCT/EP2018/067867, filed Jul. 3, 2018, which was published under PCT Article 21(2) and which claims priority to European Application No. 17180569.0, filed Jul. 10, 2017, which are all hereby incorporated in their entirety by reference.

TECHNICAL FIELD

The present invention pertains to a process for manufacturing a mixture of straight-chain higher ethyleneamines and non-straight-chain higher ethyleneamines or urea derivatives thereof. Non-straight-chain higher ethyleneamine are branched higher ethyleneamines and cyclic higher ethyleneamines.

BACKGROUND

Ethyleneamines consist of two or more nitrogen atoms linked by ethylene units. Straight-chain ethyleneamines can be represented by the formula H2N(—CH2-CH2-NH)p-H. For p=1, 2, 3, 4, . . . this gives, respectively, ethylenediamine (EDA), diethylenetriamine (DETA), linear triethylenetetramine (L-TETA), and linear tetraethylenepentamine (L-TEPA). It is clear that this range can be extended. With three or more ethylene units it is also possible to create branched ethyleneamines such as N(CH2-CH2-NH2)3, tri-saminoethylamine (TAEA). Cyclic ethylenamines are formed when two adjacent ethylene units are connected by two nitrogen atoms to form a cyclic piperazine ring —N((CH2-CH2)2)N—. Examples of cyclic ethyleneamines are piperazine and aminoethylpiperazine.

Ethyleneamines, in particular higher ethyleneamines are attractive products from a commercial point of view. The term "higher ethyleneamines" refers to ethyleneamines containing three or more ethylene units. In particular, the interest in higher ethyleneamines is increasing as these compounds have numerous commercial applications, e.g., as starting materials for, or use in, asphalt additives, corrosion inhibitors, epoxy curing agents, fabric softeners, fuel additives, hydrocarbon purification, ion exchange resins, lube oil additives, paper wet-strength resins, petroleum production chemicals, solvents, synthetic resins such as polyamide resins, mineral processing aids and interface-active substances (surfactants).

The main industrial-scale process for producing mixtures of straight-chain and non-straight-chain higher ethyleneamines is the so-called EDC process, in which ethylenedichloride is reacted with aqueous ammonia and/or another ethyleneamine at elevated temperatures and pressures to form hydrochloride salts of the ethyleneamines. The hydrochloride salts are treated with caustic to obtain the ethylene amine compounds. The reaction product comprises ethylenediamine, diethylenetriamine, piperazine, and a mixture of higher linear, branched, and cyclic higher ethyleneamines Reference is made to, e.g., IHS Chemical, Ethyleneamines, Chemical Economics Handbook, T. Kumamoto et al, (2005), p. 15. Reference can also be made to pages 2 and 3 of WO2011/107512.

The EDC process has a number of disadvantages. It is fully dependent on the use of ethylenedichloride which is toxic, highly flammable, carcinogenic, expensive, and difficult to handle and therefore not always and everywhere available. It further generated large amounts of NaCl, which may result in corrosion and the formation of colored side products, which may create a need for additional purification steps such as distillation or bleaching. Additionally, it is accompanied by the production of vinylchloride which is also a hazardous material.

A particular disadvantage of the EDC process is that it is difficult to tailor the ratio between the compounds formed. Specifically, it has been found that, irrespective of the composition of the starting materials, straight-chain starting materials will be converted to branched and cyclic products, whether this is desired or not.

There is need in the art for a process which makes it possible to prepare tailor-made mixtures of straight-chain and non-straight-chain higher ethyleneamines There is further need in the art for a process which addresses the other disadvantages of the EDC process. The present invention provides a process which addresses these problems.

BRIEF SUMMARY

A process for manufacturing a mixture of straight-chain higher ethyleneamines and non-straight-chain higher ethyleneamines selected from branched higher ethyleneamines and cyclic higher ethyleneamines, or the urea derivatives thereof, includes reacting an amine-functional compound with an ethanolamine-functional compound in the presence of a carbon oxide delivering agent, wherein a) an amine-functional compound comprises a combination of straight-chain amine-functional compound and non-straight-chain amine-functional compound and is reacted with straight-chain ethanolamine-functional compound, or b) a straight-chain amine-functional compound is reacted with ethanolamine-functional compound comprising a combination of straight-chain ethanolamine-functional compound and non-straight-chain ethanolamine-functional compound, or c) an amine-functional compound comprising a combination of straight-chain amine-functional compound and non-straight-chain amine-functional compound is reacted with ethanolamine-functional compound comprising a combination of straight-chain ethanolamine-functional compound and non-straight-chain ethanolamine-functional compound.

DETAILED DESCRIPTION

The present invention pertains to a process for manufacturing a mixture of straight-chain higher ethyleneamines and non-straight-chain higher ethyleneamines selected from branched higher ethyleneamines and cyclic higher ethyleneamines, at least in part in the form of urea derivatives thereof, comprising the step of reacting amine-functional compound with ethanolamine-functional compound in the presence of a carbon oxide delivering agent, wherein
a) amine-functional compound comprising a combination of straight-chain amine-functional compound and non-straight-chain amine-functional compound is reacted with straight-chain ethanolamine-functional compound, or
b) straight-chain amine-functional compound is reacted with ethanolamine-functional compound comprising a combination of straight-chain ethanolamine-functional compound and non-straight-chain ethanolamine-functional compound, or c) amine-functional compound comprising a combination of straight-chain amine-functional compound and non-straight-chain amine-functional compound is reacted with ethanolamine-functional compound comprising a combination of straight-chain ethanolamine-functional compound and non-straight-chain ethanolamine-functional compound.

It has been found that the process according to the invention makes it possible to prepare tailor-made mixtures of straight-chain and non-straight-chain higher ethyleneamines, or urea derivatives thereof. Further advantages of the present invention and specific embodiments thereof will become clear from the further specification.

A key feature of the process of the present invention is it has been found that in the process of reacting amine-functional compound with ethanolamine-functional compound in the presence of a carbon oxide delivering agent, the configuration of the —NX-CH2-CH2-NX-moieties (wherein X is independently hydrogen or an alkylene connection to another part of the molecule) in the reactants is relatively stable. That is, cyclization or decyclization and branching or debranching take place to a relatively limited extent. This is different from the EDC route, where cyclization and branching occur in substantial percentages. The present inventors have now recognized that this stability of the configuration of the —NX-CH2-CH2-NX— moieties in the reactants makes it possible to obtain a tailored product composition by proper selection of the starting materials. This makes it possible to recreate commercially available mixtures of straight-chain higher ethyleneamines and non-straight-chain higher ethyleneamines via an attractive process. It also makes it possible to create new mixtures of straight-chain higher ethyleneamines and non-straight-chain higher ethyleneamines for specific new uses.

Incidentally, it is noted that U.S. Pat. No. 4,503,250 describes a process for preparing polyalkylene polyamines by reacting ammonia or an alkyleneamine compound having two primary amine groups or mixtures thereof with an alcohol or an alkanolamine compound having a primary amino group and a primary or secondary hydroxyl group or mixtures thereof in the presence of a derivative of carbonic acid. This reference focuses on the manufacture of predominantly linear polyalkylene polyamines.

The invention will be discussed in more detail below.

In the process of the present invention the amine-functional compound reacts with the ethanolamine-functional compound. As will be clear to the skilled person, a mixture of straight-chain higher ethyleneamines and non-straight-chain higher ethyleneamines will only be obtained when a straight-chain compound is reacted with a mixture of straight-chain and non-straight-chain compounds, or a mixture of straight-chain and non-straight-chain compounds is reacted with another mixture of straight-chain and non-straight-chain compounds.

Therefore, the following combinations of starting materials are possible in the present invention:

a) amine-functional compound comprising a combination of straight-chain amine-functional compound and non-straight-chain amine-functional compound is reacted with straight-chain ethanolamine-functional compound, or b) straight-chain amine-functional compound is reacted with ethanolamine-functional compound comprising a combination of straight-chain ethanolamine-functional compound and non-straight-chain ethanolamine-functional compound, or c) amine-functional compound comprising a combination of straight-chain amine-functional compound and non-straight-chain amine-functional compound is reacted with ethanolamine-functional compound comprising a combination of straight-chain ethanolamine-functional compound and non-straight-chain ethanolamine-functional compound.

Within the context of the present specification, the term amine-functional compound refers to an ethylene amine compound comprising at least two amine groups connected through an ethylene unit with the compound not comprising hydroxyl groups. The term ethanolamine-functional compound refers to an ethylene amine compound comprising at least one hydroxyl group and at least one amine group with at least one hydroxyl group being connected to a primary or secondary amine group through an ethylene unit. The term higher ethyleneamines refers to ethyleneamines containing three or more ethylene units. The carbon oxide delivering agent is selected from the group of carbon dioxide, urea, alkyl ureas, linear and cyclic alkylene ureas, linear and cyclic carbamates, and organic carbonates. These compounds are discussed in more detail below.

As indicated above, the term amine-functional compound refers to an ethylene amine compound comprising at least two amine groups connected through an ethylene unit with the compound not comprising hydroxyl groups. In a preferred embodiment the amine-functional compound contains at least two primary amine groups, and optionally more amine groups that may be primary, secondary and/or tertiary amines wherein the amine groups within the compound are linked to one another via ethylene groups, and optionally some by a carbonyl moiety (to give a urea unit in the amine-functional compound).

The term ethanolamine-functional compound refers to an ethylene amine compound comprising at least one hydroxyl group and at least one amine group with at least one hydroxyl group being connected to a primary or secondary amine group through an ethylene unit. In one embodiment, the ethanolamine-functional compound contains at least one hydroxyl group and at least one primary amine groups, and optionally more amine groups that may be primary, secondary and/or tertiary amines wherein the amine groups within the compound are linked to one another via ethylene groups, and optionally some by a carbonyl moiety (to give a urea unit in the amine-functional compound).

Within the context of the present specification non-straight-chain amine compounds, whether they are amine-functional compounds or ethanolamine-functional compounds, comprise branched amine compounds and cyclic amine compounds. Branched amine compounds are, in particular, compounds comprising at least one nitrogen atom connected to three ethylene units, i.e., a tertiary amine moiety. Cyclic amine compounds are, in particular, compounds comprising a piperazine structure:

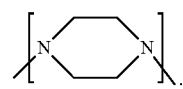

There are also amine compounds which comprise both a branched moiety and a cyclic moiety. Within the context of the present specification these compounds will be encompassed within the group of cyclic compounds, unless it clear from the context that they are not meant to be encompassed. Unless specifically indicated otherwise, cyclic compounds may encompass mixtures of cyclic compounds, branched compounds may encompass mixtures of branched compounds, and non-straight-chain compounds may encompass mixtures of cyclic compounds, mixtures of branched compounds, and mixtures of cyclic and branched compounds.

In one embodiment of the present invention the amine-functional starting material comprises non-straight-chain amine-functional compound comprising a cyclic amine-functional compound selected from the group of piperazine or an ethylene-amine derivative of piperazine such as aminoethylpiperazine (AEP), diaminoethylpiperazine (DAEP), piperazinoethylpiperazine (PEP), piperazino-ethylethylenediamine (PEEDA), and mixtures thereof.

The use of piperazine and/or aminoethylpiperazine as cyclic amine-functional compound is considered preferred.

In one embodiment of the present invention the amine-functional starting material comprises non-straight-chain amine-functional compound comprising a branched amino-functional compound comprising at least one tertiary nitrogen atom. Examples of suitable branched amine-functional compounds are compounds of the formula

N(CH2-CH2-(NH-CH2-CH2)n-NH2)3, wherein each n independently is 0 or an integer, in particular 1, 2, 3, or 4, for example, triaminoethylamine, aminoethyltriethylenetetramine, or mixtures thereof. The use of triaminoethylamine as branched amine-functional compound is preferred.

In one embodiment, the straight-chain amine-functional compound comprises one or more compounds of the formula H2N—(CH2-CH2-NH)qH, wherein q is at least 1, in particular in the range of 1 to 10, more in particular 1 to 5, e.g., compounds selected from the group of ethylenediamine (EDA), diethylenetriamine (DETA), triethylenetetramine (L-TETA), tetraethylenepentamine (L-TEPA), and mixtures thereof.

In one embodiment the non-straight-chain ethanolamine-functional compound comprises a cyclic ethanolamine-functional compound, e.g., selected from the group of hydroxyethyl derivatives of aminoethylpiperazine (AEP) such as piperazinoethylmonoethanolamine (PEMEA), etc.

In one embodiment the non-straight-chain ethanolamine-functional compound comprises a branched ethanolamine-functional compound comprising at least one tertiary nitrogen atom, for example a compound of the formula N[(CH2-CH2-(NH-CH2-CH2)n-OH)]m[(CH2-CH2-(NH-CH2-CH2)r-NH2)]3-m, wherein m is 1, or 2, or 3, each n independently is an integer, in particular 1, 2, 3, or 4, and each r independently is 0 or an integer, in particular 1, 2, 3, or 4.

A first example of a suitable compound of this formula is a compound wherein m is 1, n is 1, and r is 0: N(CH2-CH2-NH-CH2-CH2-OH)(CH2-CH2-NH2)]2

This is a preferred compound in this embodiment of the invention.

A further example of a suitable compound of the above formula is a compound wherein m is 2, n is 1, and r is 1: N(CH2-CH2-NH-CH2-CH2-OH)2(CH2-CH2-NH-CH2-CH2-NH2).

In one embodiment, the straight-chain ethanolamine-functional compound comprises compounds of the formula HO—(CH2-CH2-NH)y-H wherein y is at least 1, in particular in the range of 1 to 10, more in particular 1 to 5, e.g., compounds selected from the group of monoethanolamine (MEA), aminoethylethanolamine (AEEA), and hydroxyethyldiethylenetriamine (HE-DETA). The use of monoethanolamine (MEA) and/or aminoethylethanolamine (AEEA) may be preferred.

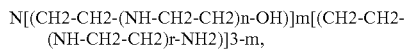

It may be preferred in the present invention to react an amine-functional compound comprising a combination of straight-chain amine-functional compound and non-straight-chain amine-functional compound with straight-chain ethanolamine-functional compound. This is because non-straight-chain amine-functional compounds may have a higher availability than non-straight-chain ethanolamine-functional compounds.

A preferred embodiment would be the reaction of straight-chain amine-functional compound and non-straight-chain amine-functional compound with straight-chain ethanolamine-functional compound selected from monoethanolamine (MEA) and/or aminoethylethanolamine (AEEA). For preferences for the straight-chain amine-functional compound and the non-straight-chain amine-functional compound, reference is made to what is stated above.

In general, in the process according to the invention, the total amount of non-straight-chain amine-functional compound and non-straight-chain ethanolamine-functional compound is between 10 and 90 mole % of the total amount of amine-functional compound and ethanolamine-functional compound. If the total amount of non-straight-chain starting compounds is below 10 mole % of the total amount of starting compound, the amount of non-straight-chain compounds formed in the reaction will be so low that its presence generally will not have technical relevancy. Conversely, if the total amount of non-straight-chain starting compounds is above 90 mole % of the total amount of starting compound, the amount of straight-chain compounds formed in the reaction will be so low that its presence generally will not have technical relevancy. The optimum ratio between the various components will depend on the desired end product. Some further guidance on this issue will be provided below for specific end products. Otherwise it is within the scope of the skilled person to determine the ratio between straight-chain and non-straight-chain starting materials from the desired composition of the product. This is because, as has been indicated above, it has been found that in the process according to the invention cyclization/decyclization and branching/debranching take place to a relatively limited extent. Therewith, the desired degree of cyclic compounds and branched compounds in the product provides guidance for the degree of cyclic compounds and branched compounds in the starting materials.

It thus is a feature of the present invention that the ratio of the total amount of piperazine moieties in the starting materials to the total amount of piperazine moieties in the mixture resulting from the reaction generally is in the range of 0.7:1 to 1.3:1, in particular in the range of 0.8:1 to 1.2:1, more in particular in the range of 0.9:1 to 1.1:1. This reflects that in the process according to the invention the cyclization/decyclization is limited. The starting material is the total of amine-functional compound and ethanolamine-functional compound.

It is a further feature of the present invention that the ratio of the total amount of tertiary amine moieties of the formula N(CH2-CH2-)3 in the starting material to the total amount of tertiary amine moieties of the formula N(CH2-CH2-)3 in the mixture resulting from the reaction generally is in the range of 0.7:1 to 1.3:1, in particular in the range of 0.8:1 to 1.2:1, more in particular in the range of 0.9:1 to 1.1:1. This reflects that in the process according to the invention the branching/debranching is limited.

In the process of the invention amine-functional compound is reacted with ethanolamine-functional compound in the presence of a carbon oxide delivering agent.

The carbon oxide delivering agent is a compound containing a carbonyl moiety that can be transferred to an ethanolamine-functional compound leading to the formation of a cyclic carbamate, such as CMEA (2-oxazolidinone) or that can be transferred to an ethyleneamine (EA) leading to the formation of the corresponding cyclic ethylene urea (UEA). Next to cyclic compounds, linear carbamates and ureas may form as well.

Carbon oxide delivering agents within the scope of the present invention include carbon dioxide, and organic compounds in which a carbonyl moiety is available for being transferred as described above. More specifically, the carbon oxide delivering agent is selected from the group of carbon dioxide, urea, alkyl ureas, linear and cyclic alkylene ureas, linear and cyclic carbamates, and organic carbonates. Organic compounds in which a carbonyl moiety is available include urea and derivatives thereof; linear and cyclic alkylene ureas, especially cyclic urea, mono or di-substituted alkylene ureas, alkyl and dialkyl ureas, linear and cyclic carbamates, organic carbonates and derivatives or precursors thereof. Such derivatives or precursors may for example include ionic compounds such as carbonate or bicarbonate salts, carbamic acids and associated salts, that can be converted, in some embodiments in situ in the process of the invention, into their non-ionic counterparts, for example into linear and cyclic carbamate or urea compounds. When such ionic compounds are used in the present invention, they are organic hydrocarbon-based carbonate, bicarbonate or carbamate salts. Preferably the CO delivering agent is CO2 or an organic compound that is suitable for use as a carbon oxide delivering agent and wherein alkylene is ethylene, or urea or ethylene carbonate, more preferably the carbon oxide delivering agent is at least partly added as carbon dioxide or urea. The carbon oxide delivering agent can be present in the process in the same molecule as the amine-functional or the ethanolamine-functional compound by using the aforementioned urea or carbamate compounds.

Examples of carbon oxide delivering agents include

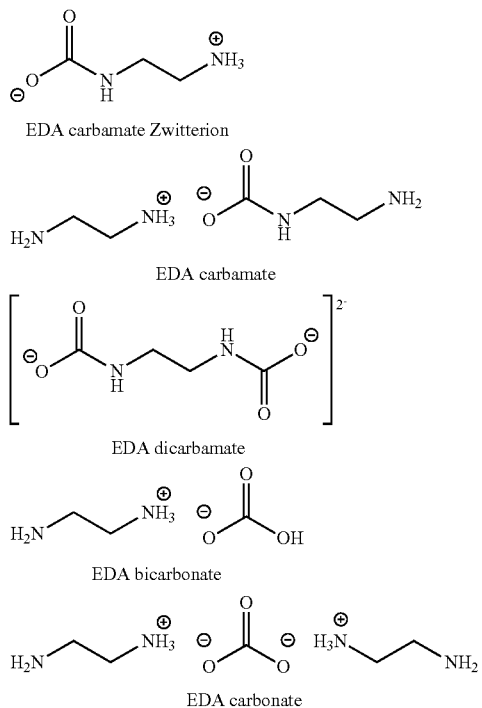
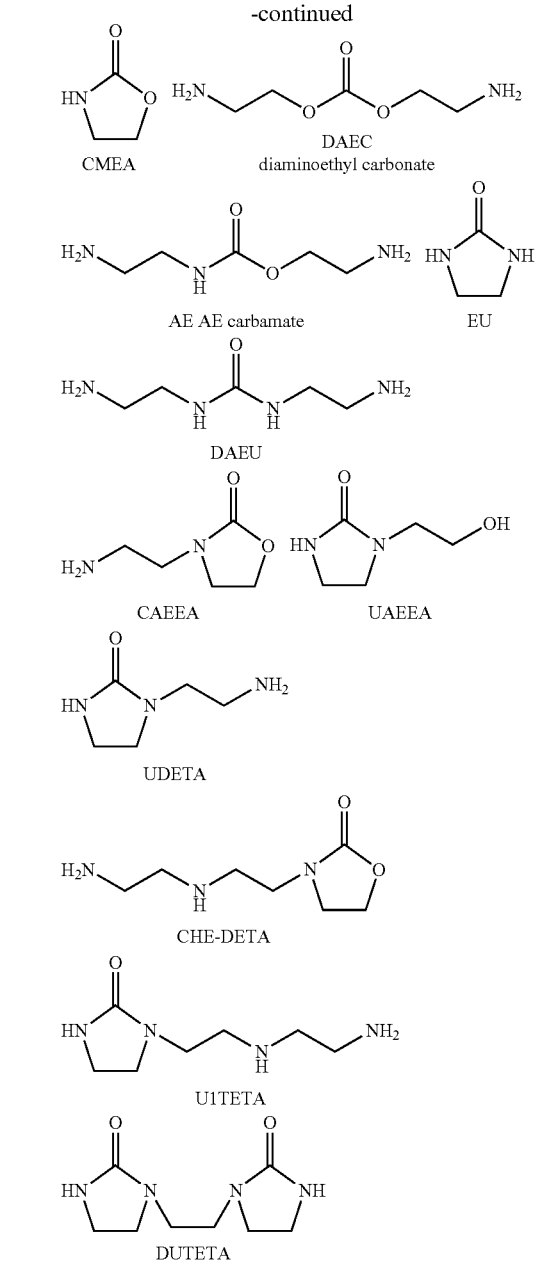

In the above drawing CAEEA again stands for the carbamate of aminoethylethanolamine, UDETA for the urea of diethylene triamine, DAEU stands for diaminoethyl urea, AE AE carbamate stands for amino ethyl aminoethanol carbamate, CHE-DETA stands for the carbamate of hydroxyethyldiethylene triamine, U1TETA stands for the terminal monourea of triethylene tetramine, and DUTETA stands for the 1,3-diurea of triethylene tetramine.

The carbon oxide delivering agent is most preferably added to the reaction in the form of carbon dioxide, the carbamate derivative of the ethanolamine-functional compound or the urea derivative of the amine-functional compound, or a combination of these. Heating a suitable mixture of an ethanolamine, an amine that is not tertiary and a carbon oxide delivering agent to a relatively high temperature provides a way to produce a higher amine and CO containing derivative thereof that can serve as a carbon oxide delivering agent.

It is preferred for the carbon oxide delivering agent to be provided at least in part as one compound with the ethanolamine-functional compound and/or the amine-functional compound in the form of a CO adduct, e.g., an adduct comprising a cyclic ethylene urea unit

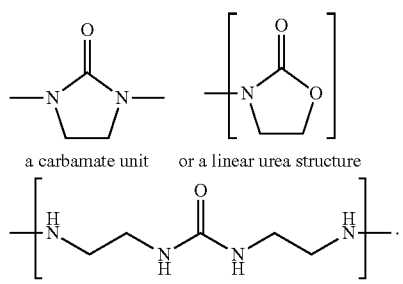

a carbamate unit or a linear urea structure

The reaction between the amine-functional compound and the ethanolamine-functional compound is carried out by combining the various components and bringing the mixture to reaction conditions.

Reaction conditions include a reaction temperature which is generally at least 100° C., in particular at least 150° C. The temperature preferably is at least 180° C., more in particular at least 200° C. In some embodiments the use of higher temperatures may be preferred, e.g., at least 230° C., or even at least 250° C. The reaction temperature generally is at most 400° C., in particular at most 360° C., in some embodiments at most 340° C. It has been found that higher temperatures favor the conversion to ethyleneamine compounds.

The reaction is carried out at a pressure which is such that the reaction mixture is in the liquid phase. It will therefore depend on the reaction temperature. In general, the reaction pressure will be between 1 and 60 bar.

The reaction time during the process is in an embodiment between 5 minutes and 40 hours, preferably between 0.25 and 25 hours or between 0.5 and 25 hours, more preferably between 0.5 and 18 hours or between 1 and 18 hours.

The process of the present invention can be done with or without any additional liquid present. If a liquid is added to the reaction system, the liquid preferably is a polar liquid, such as an alcohol or water. Doing the process of the present invention in the presence of water as a liquid or without any additional liquid is preferred.

The reactor employed can be any suitable reactor including continuously stirred tank reactor, pipeline reactor, tubular or multi-tubular reactor. The reactor may be adiabatic or equipped with external or internal heating devices. Feed may be single point or split into multiple points. It can consist of multiple stages with inter-stage heat exchange.

The process can be carried out in a batch reactor, possibly fed-batch operation, or in a continuously operating system in one reactor or in a cascade of continuous flow reactors. The reactor can be a single reaction unit or a set of reaction units. The reaction and separation can be performed in separate steps or at least partially simultaneously. The reaction and separation can involve multiple reaction steps with separation steps in between.

In the large-scale production of chemicals it is preferred to employ a continuous process. The continuous process may be, for example, a single-pass or a recycle process. In a single-pass process, one or more of the reagents pass through the process equipment once, and then the resulting effluent from the reactor is sent for purification or further processing.

The person skilled in the art is capable of selecting the proper reactor and separation unit scheme by determining the overall yield, energy consumption and waste production.

The product mixture resulting from the reaction can be further processed or fractionated into several products that each independently are either pure compounds or mixture of compounds, some of which may be recycled.

The reaction product will comprise one or more compounds in the form of urea adducts. In one embodiment, the product is subjected to a CO removal reaction to convert the urea adduct into amine compounds. Within the context of the present specification, a CO removal reaction is intended to refer to any reaction wherein the urea adduct is converted into the corresponding amine compound by removal of the carbonyl group and addition of two hydrogen atoms. This can be done using methods known in the art, e.g., by reaction with caustic compounds such as NaOH.

The present invention is particularly suitable for manufacturing tailored compositions of higher ethyleneamines.

In one embodiment, the present invention pertains to a process for manufacturing a triethylenetetramine composition that is compatible with the current REACH definition for this product, or the urea-containing precursor of such product. Therefore, in one embodiment, the present invention pertains to a process for manufacturing a composition comprising, calculated on the total amount of triethylenetetramine, 50-90 wt. % straight-chain triethylenetetramine, 0-50 wt. % of cyclic triethylenetetramine, and 0-20 wt. % of branched triethylenetetramine, or urea derivatives thereof, comprising the step of reacting an amine-functional compound with an ethanolamine-functional compound in the presence of a carbon oxide delivering agent, wherein the amine-functional compound is a combination of ethylenediamine (EDA) and piperazine (PIP) and the ethanolamine-functional compound is aminoethylethanolamine (AEEA), or the amine-functional compound is a combination of diethylenetriamine (DETA) and a cyclic compound selected from aminoethylpiperazine (AEP) and piperazine (PIP) and the ethanolamine-functional compound is monoethanolamine (MEA), wherein the amount of cyclic compound is selected such that the product from the reaction comprises, calculated on the total amount of triethylenetetramine, 50-90 wt. % straight-chain triethylenetetramine, 0-50 wt. % of cyclic triethylenetetramine, and 0-20 wt. %. of branched triethylenetetramine, or urea derivatives thereof.

As the process according to the invention is characterised by a high stability in that the cyclic moieties and branched moieties in the starting material end up in the product, it is within the scope of the skilled person to select the amount of cyclic material in the starting material to end up with the desired amount of cyclic material in the product.

In general, the amount of branched material in the product in this embodiment will be in the range of 0-10 wt. %, in particular in the range of 0-5 wt. %, more in particular in the range of 0-2 wt. %.

In the above, and in the REACH specification the term cyclic triethylenetetramine is intended to refer to a compound which comprises a linear triethylenetetramine chain wherein two adjacent ethylene units are connected through an additional nitrogen atom. Therefore, cyclic triethylenetetramine contains four amine moieties, and depending on the number of cyclic moieties, four or five ethylene moieties.

In one embodiment, the product comprises 0-30 wt. % of diaminoethylpiperazine (DAEP) and 0-20 wt. % of piperazinoethylethylenediamine (PEEDA), or urea derivatives thereof, calculated on total triethylenetetramine.

In a further embodiment, the invention pertains to a process for manufacturing a triethyleneteramine (TETA) composition that is comparable with commercially available TETA compositions. Therefore, in one embodiment, the present invention pertains to a method for manufacturing a composition comprising, calculated on the total amount of TETA, 40-80 wt. %, in particular 50-75 wt. %, more in particular 60-70 wt. % of straight-chain triethylenetetramine, 15-50 wt. %, in particular 20-40 wt. %, more in particular 20 to 35 wt. % of cyclic triethylenetetramine, and 0-10 wt. % of branched triethylenenetetramine, or urea derivatives thereof, by selecting the starting materials as described above in such amounts that a product with the described composition is obtained.

In one embodiment, the present invention pertains to a process for manufacturing a tetraethylenepentamine (TEPA) composition that can be compatible with the current REACH definition for this product, or a urea-containing precursor of such a product. Therefore, in one embodiment, the present invention pertains to a process for manufacturing a composition comprising, calculated on total TEPA, 30-70 wt. % straight-chain tetraethylenepentamine, 0-30 wt. % branched tetraethylenepentamine, and 0-50 wt. % of cyclic tetraethylenepentamine, or urea derivatives thereof.

Analogous to cyclic triethylenetetraamine above, cyclic tetraethylenepentamine refers to compounds which comprise a linear tetraethylenepentamine chain wherein two adjacent ethylene units are connected through an additional nitrogen atom. Therefore, cyclic tetraethylenepentamine contains five amine moieties, and depending on the number of cyclic moieties, five or six ethylene moieties.

REACH-compatible TEPA compositions, or the urea derivative thereof, can, e.g., be obtained from the following combinations of starting materials:
1) the amine-functional compound comprises a combination of diethylenetriamine (DETA) and aminoethylpiperazine (AEP) and the ethanolamine-functional compound comprises aminoethylethanolamine (AEEA). This embodiment is considered preferred because good results are obtained.
2) the amine-functional compound comprises a combination of ethylenediamine (EDA) and aminoethylpiperazine (AEP) and the ethanolamine-functional compound comprises a combination of monoethanolamine (MEA) and aminoethylethanolamine (AEEA).
3) the amine-functional compound comprises a combination of ethylenediamine (EDA) and piperazine (PIP) and the ethanolamine-functional compound comprises a combination of monoethanolamine (MEA) and aminoethylethanolamine (AEEA). This embodiment may be attractive because the starting materials are relatively widely available.
4) the amine-functional compound comprises a combination of ethylenediamine (EDA) and piperazine (PIP) and the ethanolamine-functional compound comprises hydroxyethyldiethylenetriamine (HE-DETA).
5) the amine-functional compound comprises a combination of one or more linear compounds selected from the group of diethylenetriamine (DETA) and triethylenetetraamine (L-TETA), and one or more non-straight-chain compounds selected from the group of branched triethylenetetraamine (T-TETA), diaminoethylpiperazine (DAEP), piperazinoethylethylenediamine (PEEDA), aminoethylpiperazine (AEP), and piperazine (PIP), and the ethanolamine-functional compound is monoethanolamine (MEA).

In all cases, the relative amounts of straight-chain and non-straight-chain compounds are to be selected such that the final composition meets the requirements above. Again, as the process according to the invention is characterised by a high stability in that the cyclic moieties and branched moieties in the starting material end up in the product from the reaction, it is within the scope of the skilled person to select the amount of cyclic material in the starting material to end up with the desired amount of cyclic material in the product.

In one embodiment, the process according to the invention is used to manufacture a TEPA composition comprising, calculated on the total amount of TEPA, 30-70 wt. %, in particular 40 to 60 wt. %, more in particular 45-55 wt. % of linear TEPA, 15-50 wt. %, in particular 20-40 wt. %, more in particular 25-35 wt. % of cyclic TEPA, and 0-30 wt. %, in particular 10-20 wt. % of branched TEPA.

Based on the teachings above it will be clear to the skilled person how to select the starting materials such that the claimed compositions are obtained.

In the present specification, mention is made of urea adducts and urea derivatives. These terms are used interchangeably to refer to compounds wherein two nitrogen atoms are connected through a —C(O)— moiety.

The present invention will be elucidated by the following examples, without being limited thereto or thereby.

Comparative Examples A, B (Reductive Amination of MEA, and PIP and MEA)

55 g (0.90 mol) monoethanolamine (MEA) (Example A) or a mixture consisting of 49.5 g (0.81 mol) MEA and 5.5 g (0.06 mol) piperazine (PIP) (Example B) were added to a high pressure autoclave containing 8.16 g $H_2O$ and 10 g of a 10 wt. % $Ni/Al_2O_3$ catalyst. After sealing the autoclave lid and inerting with $N_2$ 70 g of anhydrous NH3 was added and the autoclave was subsequently pressurized with $H_2$ to a pressure of 82 bar. The temperature was then raised to 194° C. and kept there for 240 min. After cooling a sample was analyzed using gas chromatography coupled with a flame ionization detector (GC-FID).

TABLE 1

| | Example | |
|---|---|---|
| | A | B |
| PIP content in wt. % in starting material | 0.0 | 10.0 |
| Product composition | | |
| MEA | 42.0 | 39.6 |
| PIP | 6.2 | 14.6 |
| AEP | 0.9 | 1.0 |
| HEP | 0.3 | 0.2 |
| PEEDA | 0.2 | n.d. |
| non-cyclic EA | 42.0 | 39.4 |

All GC-FID data in wt. % (normalized)
n.d. = not detected

AEP stands for aminoethylpiperazine, HEP stands for hydroxyethylpiperazine, PEEDA stands for piperazinoethylethylenediamine Non-cyclic EA denotes the sum of all ethyleneamines like EDA, DETA, TETA etc. which do not contain a piperazine moiety.

The catalytic reductive amination of MEA—without added PIP—results in the formation of 6.2 wt. % of PIP. When the same reaction is performed starting with 10 wt. % of PIP in MEA, 14.6 wt. % of PIP are found.

Conclusion: PIP is formed during the catalytic reductive amination of MEA using ammonia. When PIP is added to MEA, it does not react in significant amounts to form higher cyclic ethylene amines (such as PEEDA or AEP).

Examples 1a-1c: Reaction of UAEEA, EU and EDA with PIP

The urea derivative of aminoethylethanolamine (UAEEA), ethyleneurea (EU, the urea derivative of ethylenediamine), ethylenediamine (EDA) and piperazine (PIP) were added to a microwave vial in the respective amounts as indicated in Table 2. The vial was capped, flushed with Na, and heated at 280° C. for 4 h. The sample was then allowed to cool and the content was analyzed by GC-FID.

TABLE 2

| | Example | | |
|---|---|---|---|
| | 1a | 1b | 1c |
| reactants | UAEEA/EU/EDA | UAEEA/EU/EDA/PIP | UAEEA/EU/EDA/PIP |
| reactant amounts in g | 0.80/0.52/0.36 | 0.80/0.52/0.27/0.13 | 0.70/0.23/0.32/0.23 |
| molar ratio of reactants | 1:1:1 | 1:1:0.75:0.25 | 1:0.5:1:0.5 |
| amount of PIP in reactants in wt. % | 0 | 7.5 | 15.5 |
| amount of PIP-moieties in products in wt. % | 0.9 | 7.4 | 15.5 |
| PIP-moieties (products):PIP (reactants) in % | n.a. | 98 | 100 |
| EDA | 16.3 | 13.4 | 14.5 |
| PIP | 0.4 | 3.2 | 9.0 |
| AEEA | 1.8 | 1.7 | 4.0 |
| EU | 20.0 | 19.6 | 12.8 |
| L-TETA | 0.3 | n.d. | 0.3 |
| UDETA | 0.7 | 0.4 | n.d. |
| UAEEA | 18.5 | 19.3 | 22.6 |
| Sum (U)TETA | 30.0 | 20.1 | 14.8 |
| UPEEDA (PIP-moiety) | 1.2 (0.5) | 9.6 (4.2) | 14.9 (6.5) |

All GC-FID data in wt. %
n.d. = below detection limits
Sum (U)TETA denotes the sum of L-TETA and urea adducts thereof Conclusion: PIP which is added to a reactant mixture containing UAEEA, EU and EDA is mainly converted to UPEEDA, a cyclic higher ethyleneamine. The ratio between the amount of piperazine moieties in the product versus the amount of piperazine moieties in the starting materials shows that the amount of piperazine groups has not changed.

Examples 2a and 2b

EU, EDA, the carbamate derivative of monoethanolamine (CMEA), and AEP were added to a microwave vial in the respective amounts as indicated in Table 2. The vial was capped, flushed with $N_2$, and heated at 260° C. for 4 h. The sample was then allowed to cool and the content was analyzed by GC-FID.

TABLE 3

| | Example | |
|---|---|---|
| | 2a | 2b |
| reactants | EU/EDA/CMEA | EU/EDA/CMEA/AEP |
| reactant amounts in g | 0.35/0.24/1.04 | 0.35/0.02/1.04/0.46 |

TABLE 3-continued

| | Example | |
|---|---|---|
| | 2a | 2b |
| molar ratio of reactants | 1:1:3 | 1:0.1:3:0.9 |
| amount of AEP in wt. % | 0 | 30.3 |
| amount of AEP-moieties in products in wt. % | 0.4 | 31.0 |
| piperazine moieties (products):piperazine moieties (reactants) in % | n.a. | 102 |
| EDA | 4.9 | 4.8 |
| AEP | n.d. | 3.4 |
| PIP | n.d. | 0.3 |
| EU | 24.5 | 20.6 |
| UDETA | 13.9 | 6.9 |
| UAEEA | 22.8 | 6.1 |
| Sum (U)TETA | 25.6 | 9.1 |
| DAEP (AEP-moiety)) | n.d. | 9.7 (7.2) |
| UPEEDA (AEP-moiety) | 0.4 (0.2) | 4.8 (3.1) |
| other cyclic TEPA compounds (AEP-moiety) | 0.4 (0.2) | 32.2 (17.2) |
| Sum (U)TEPA | 7.6 | 2.1 |

All GC-FID data in wt. % (normalized)
n.d. = below detection limits
Sum (U)TETA denotes the sum of L-TETA and urea adducts thereof
Sum (U)TEPA denotes the sum of L-TEPA and urea adducts thereof
UPEEDA stands for the urea derivative of piperazinoethylethylenediamine.

Conclusion: AEP which is added to a reactant mixture containing EU and EDA and CMEA is mainly converted to DAEP, UPEEDA, and further cyclic TEPA compounds. The ratio between the amount of aminoethylpiperazine moieties in the product versus the amount of aminoethylpiperazine moieties in the starting materials shows that the amount of aminoethylpiperazine groups has not changed substantially.

Examples 3a-b

EU, EDA, UAEEA and AEP were added to a microwave vial in the respective amounts as indicated in Table 4. The vial was capped, flushed with $N_2$, and heated at 280° C. for 4 h. The sample was then allowed to cool and the content was analyzed by GC-FID.

TABLE 4

| | Example | |
|---|---|---|
| | 3a | 3b |
| reactants | EU/EDA/AEP/UAEEA | EU/EDA/AEP/UAEEA |
| reactant amounts (weight ratios) in % | 28:10:20:42 | 26:02:34:38 |
| amount of AEP in reactants in wt. % | 20.0 | 34 |
| amount of AEP-moieties in products in wt. % | 18.3 | 32.0 |
| piperazine moieties (products):piperazine moieties (reactants) in % | 92 | 94 |
| EDA | 8.6 | 2.8 |
| AEP | 11.5 | 19.0 |
| PIP | 0.4 | 0.2 |
| EU | 22.0 | 11.3 |
| AEEA | 1.5 | 0.5 |
| UDETA | 1.9 | 1.6 |
| UAEEA | 20.0 | 20.0 |
| Sum (U)(C)TETA | 22.9 | 30.3 |
| cyclic UTEPA (piperazine-moiety) | 12.7 (6.8) | 24.3 (13.0) |
| Sum (U)TEPA | 7.3 | 12.0 |
| others | 3.8 | 2.3 |

All GC-FID data in wt. % (normalized)
Sum (U)(C)TETA denotes the sum of L-TETA and urea adducts thereof and CTETAs and urea adducts thereof
Sum (U)TEPA denotes the sum of L-TEPA and urea adducts thereof Conclusion: AEP which is added to a reactant mixture containing EU, EDA and UAEEA is mainly converted to urea derivatives of cyclic TEPAs. The ratio between the amount of aminoethylpiperazine moieties in the product versus the amount of aminoethylpiperazine moieties in the starting materials shows that the amount of piperazine groups has not changed significantly.

Example 4

To test whether branched amines react in the same way as linear and cyclic amines, the reaction of N,N-diethylethylenediamine with CMEA was tested. N,N-diethylethylenediamine (DE-EDA) was chosen as model substance for a branched compound and consists of a primary amine moiety connected to a branched tertiary amine moiety via an ethylene linker.

The reaction is thought to proceed as follows:

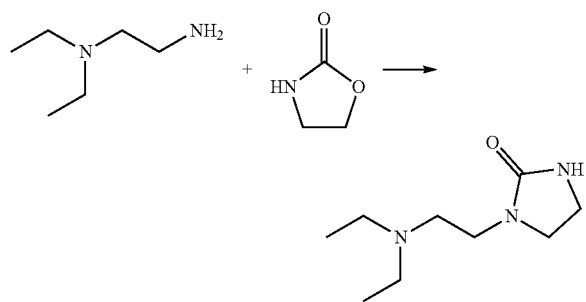

Using a molar ratio of 1:1, the reaction at 250° C. for 16 h resulted in a 50% conversion of DE-EDA and yielded 18.6 wt. % UAEEA (according to GC-FID in combination with GC coupled with mass spectroscopy)—from the reaction of MEA with CMEA—and 29.3 wt. % of the expected main reaction product—the chain extended cyclic urea of the starting material.

Conclusion: Contacting a branched compound with CMEA results in the formation of branched products. Linear or cyclic products were not detected.

Examples 5a and b

DETA or L-TETA, T-TETA, and CMEA were added to a microwave vial in the respective amounts as indicated in Table 5. The vial was capped, flushed with N2, and was heated at 270° C. for 3 h. The sample was then allowed to cool and the content was analyzed by GC-FID.

TABLE 5

|  | Example | |
|---|---|---|
|  | 5a | 5b |
| reactants | DETA/ T-TETA/ CMEA | L-TETA/ T-TETA/ CMEA |
| reactant amounts (weight ratios) in % | 39:28:33 | 38:38:22 |
| amount of T-TETA in reactants in wt. % | 28.3 | 38.4 |
| amount of T-TETA-moieties in products in wt. % | 28.1 | 38.5 |
| branched moieties (products):branched moieties (reactants) in % | 99 | 100 |
| MEA | 13.0 | 12.1 |
| DETA | 9.5 | n.d. |

TABLE 5-continued

|  | Example | |
|---|---|---|
|  | 5a | 5b |
| T-TETA | 21.8 | 35.2 |
| T-TEPA | 3.6 | 2.4 |
| UT-TEPA | 5.1 | 2.0 |
| AEEA | 1.2 | n.d. |
| UDETA | 33.2 | 0.7 |
| UAEEA | 2.6 | n.d. |
| Sum (U)TETA | 4.5 | 31.7 |
| Sum branched (U)TEPA (T-TETA moiety) | 8.6 (6.3) | 4.4 (3.3) |

All GC-FID data in wt. % (normalized)
Sum (U)TETA denotes the sum of L-TETA and urea adducts thereof
Sum (U)TEPA denotes the sum of TEPA and urea adducts thereof (linear or branched)

Conclusion: T-TETA which is added to a reactant mixture containing DETA or L-TETA and CMEA is mainly converted to urea derivatives of branched TEPAs. The ratio between the amount of T-TETA moieties in the product versus the amount of T-TETA moieties in the starting materials shows that the amount of branched groups has not changed significantly.

Examples 6a and b

DETA or L-TETA, AEP, T-TETA, and CMEA were added to a microwave vial in the respective amounts as indicated in Table 6. The vial was capped, flushed with N2, and heated at 270° C. for 3 h. The sample was then allowed to cool and the content was analyzed by GC-FID.

TABLE 6

|  | Example | |
|---|---|---|
|  | 6a | 6b |
| reactants | DETA/AEP/ T-TETA/CMEA | L-TETA/AEP/ T-TETA/CMEA |
| reactant amounts (weight ratios) in % | 28:17:20:35 | 25:21:25:29 |
| amount of T-TETA in reactants in wt. % | 20.2 | 25.2 |
| amount of T-TETA-moieties in products in wt. % | 19.1 | 24.1 |
| branched moieties (products):branched moieties (reactants) in % | 95 | 96 |
| amount of AEP in reactants in wt % | 17.1 | 21.3 |
| amount of AEP-moieties in products in wt. % | 18.0 | 21.3 |
| AEP moieties (products):AEP moieties (reactants) in % | 105 | 100 |
| MEA | 9.4 | 11.5 |
| DETA | 4.4 | n.d. |
| T-TETA | 12.9 | 17.8 |
| CTETA | 6.7 | 5.2 |
| UCTETA | 2.4 | 2.1 |
| CTEPA | 0.6 | 0.2 |
| UCTEPA | 1.4 | 0.6 |
| T-TEPA | 2.7 | 2.7 |
| UT-TEPA | 5.7 | 6.2 |
| AEP | 10.6 | 15.6 |
| UDETA | 24.6 | 1.3 |
| UAEEA | 3.3 | 1.1 |
| Sum (U)TETA | 6.9 | 27.4 |
| Sum cyclic (U)TETA (AEP moiety) | 9.1 (6.4) | 7.3 (5.1) |

TABLE 6-continued

| | Example | |
|---|---|---|
| | 6a | 6b |
| Sum branched (U)TEPA (T-TETA moiety) | 8.4 (6.2) | 8.9 (6.3) |
| Sum cyclic (U)TEPA (AEP moiety) | 2.0 (1.0) | 0.8 (0.6) |

All GC-FID data in wt. % (normalized)
Sum (U)TETA denotes the sum of L-TETA and urea adducts thereof
Sum (U)TEPA denotes the sum of TEPA and urea adducts thereof (linear or branched or cyclic)

Conclusion: T-TETA and AEP which are added to a reactant mixture containing DETA (or L-TETA) and CMEA are mainly converted to urea derivatives of branched TEPAs and cyclic TETAs, respectively. The ratio between the amount of T-TETA moieties in the product versus the amount of T-TETA moieties in the starting materials shows that the amount of branched groups has not changed significantly. The ratio between the amount of aminoethylpiperazine moieties in the product versus the amount of aminoethylpiperazine moieties in the starting materials shows that the amount of piperazine groups has not changed significantly.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A process for manufacturing a mixture of straight-chain higher ethyleneamines and non-straight-chain higher ethyleneamines selected from branched higher ethyleneamines and cyclic higher ethyleneamines, at least in part in the form of urea derivatives thereof, comprising:
reacting an amine-functional compound with an ethanolamine-functional compound in the presence of a carbon oxide delivering agent, wherein
a) the amine-functional compound comprises a combination of a straight-chain amine-functional compound and a non-straight-chain amine-functional compound and is reacted with a straight-chain ethanolamine-functional compound, or
b) a straight-chain amine-functional compound is reacted with an ethanolamine-functional compound comprising a combination of a straight-chain ethanolamine-functional compound and a non-straight-chain ethanolamine-functional compound, or
c) the amine-functional compound comprises a combination of a straight-chain amine-functional compound and a non-straight-chain amine-functional compound and is reacted with an ethanolamine-functional compound comprising a combination of a straight-chain ethanolamine-functional compound and a non-straight-chain ethanolamine-functional compound, wherein the term amine-functional compound refers to an ethylene amine compound comprising at least two amine groups connected through an ethylene unit with the compound not comprising hydroxyl groups, the term ethanolamine-functional compound refers to an ethylene amine compound comprising at least one hydroxyl group and at least one amine group with at least one hydroxyl group connected to a primary or secondary amine group through an ethylene unit, the term higher ethyleneamines refers to ethyleneamines containing three or more ethylene units, and the carbon oxide delivering agent is selected from the group of carbon dioxide, urea, alkyl ureas, linear and cyclic alkylene ureas, linear and cyclic carbamates, and organic carbonates,
wherein TETA is formed from EDA and/or DETA; PIP and/or AEP; and MEA and/or AEEA.

2. The process according to claim 1, wherein the amine-functional compound comprises a non-straight-chain amine-functional compound comprising a cyclic amine-functional compound, wherein the cyclic amine-functional compound is piperazine or an ethylene-amine derivative of piperazine.

3. The process according to claim 1, wherein the amine-functional compound comprises a non-straight-chain amine-functional compound comprising a branched amino-functional compound comprising at least one tertiary nitrogen atom, of the formula

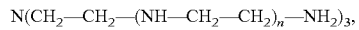

N(CH$_2$—CH$_2$—(NH—CH$_2$—CH$_2$)$_n$—NH$_2$)$_3$, wherein each n independently is 0 or an integer.

4. The process according to claim 1, wherein the straight-chain amine-functional compound comprises one or more compounds of the formula H$_2$N—(CH$_2$—CH$_2$—NH)$_q$H, wherein q is at least 1.

5. The process according to claim 1, wherein the non-straight-chain ethanolamine-functional compound comprises a cyclic ethanolamine-functional compound.

6. The process according to claim 1, wherein the non-straight-chain ethanolamine-functional compound comprises a branched ethanolamine-functional compound of the formula

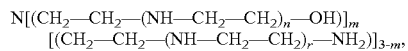

N[(CH$_2$—CH$_2$—(NH—CH$_2$—CH$_2$)$_n$—OH)]$_m$
[(CH$_2$—CH$_2$—(NH—CH$_2$—CH$_2$)$_r$—NH$_2$)]$_{3-m}$, wherein m is 1, 2, or 3, each n independently is an integer, and each r independently is 0 or an integer.

7. The process according to claim 1, wherein the straight-chain ethanolamine-functional compound comprises compounds of the formula HO—(CH$_2$-CH2-NH)$_y$—H wherein y is at least 1.

8. The process according to claim 1, wherein an amine-functional compound comprising a combination of a straight-chain amine-functional compound and a non-straight-chain amine-functional compound is reacted with a straight-chain ethanolamine-functional compound.

9. The process according to claim 1, wherein the starting materials include piperazine moieties, wherein the product includes piperazine moieties, and wherein the ratio of the total amount of piperazine moieties in the starting materials to the total amount of piperazine moieties in the product from the reaction is from about 0.7:1 to about 1.3:1.

10. The process according to claim 1, wherein the starting materials include tertiary amine moieties of the formula N(CH$_2$—CH$_2$-)$_3$, wherein the product includes tertiary amine moieties of the formula N(CH$_2$—CH$_2$-)$_3$, and wherein the ratio of the total amount of tertiary amine moieties of the formula N(CH$_2$—CH$_2$-)$_3$ in the starting material to the total amount of tertiary amine moieties of the formula N(CH$_2$—CH$_2$-)$_3$ in the product from the reaction is from about 0.7:1 to about 1.3:1.

11. A process for manufacturing a mixture of straight-chain higher ethyleneamines and non-straight-chain higher ethyleneamines selected from branched higher ethyleneamines and cyclic higher ethyleneamines, at least in part in the form of urea derivatives thereof, comprising:
reacting an amine-functional compound with an ethanolamine-functional compound in the presence of a carbon oxide delivering agent, wherein
a) the amine-functional compound comprises a combination of a straight-chain amine-functional compound and a non-straight-chain amine-functional compound and is reacted with a straight-chain ethanolamine-functional compound, or
b) a straight-chain amine-functional compound is reacted with an ethanolamine-functional compound comprising a combination of a straight-chain ethanolamine-functional compound and a non-straight-chain ethanolamine-functional compound, or
c) the amine-functional compound comprises a combination of a straight-chain amine-functional compound and a non-straight-chain amine-functional compound and is reacted with an ethanolamine-functional compound comprising a combination of a straight-chain ethanolamine-functional compound and a non-straight-chain ethanolamine-functional compound,
wherein the term amine-functional compound refers to an ethylene amine compound comprising at least two amine groups connected through an ethylene unit with the compound not comprising hydroxyl groups,
wherein the term ethanolamine-functional compound refers to an ethylene amine compound comprising at least one hydroxyl group and at least one amine group with at least one hydroxyl group connected to a primary or secondary amine group through an ethylene unit, wherein the term higher ethyleneamines refers to ethyleneamines containing three or more ethylene units, and
wherein the carbon oxide delivering agent is selected from the group of carbon dioxide, urea, alkyl ureas, linear and cyclic alkylene ureas, linear and cyclic carbamates, and organic carbonates or wherein the carbon oxide delivering agent is provided at least in part as one compound with the ethanolamine-functional compound and/or the amine-functional compound in the form of an adduct comprising a cyclic ethylene urea unit

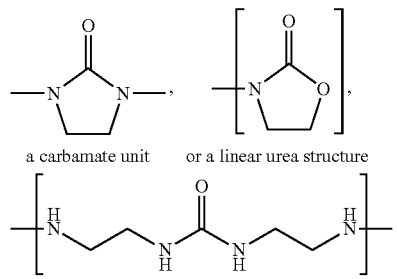

a carbamate unit    or a linear urea structure wherein TETA is formed from EDA and/or DETA; PIP and/or AEP; and MEA and/or AEEA.

12. The process according to claim 1 wherein the mixture of straight-chain higher ethyleneamines and non-straight-chain higher ethyleneamines selected from branched higher ethyleneamines and cyclic higher ethyleneamines, at least in part in the form of urea derivatives thereof, comprises, calculated on the total amount of triethylenetetramine, 50-90 wt. % straight-chain triethylenetetramine, 0-50 wt. % of cyclic triethylenetetramine, and 0-20 wt. % of branched triethylenetetramine, or urea derivatives thereof, and the process comprises reacting an amine-functional compound with an ethanolamine-functional compound in the presence of a carbon oxide delivering agent, wherein
the amine-functional compound is a combination of ethylenediamine (EDA) and piperazine (PIP) and the ethanolamine-functional compound is aminoethylethanolamine (AEEA), or
the amine-functional compound is a combination of diethylenetriamine (DETA) and a cyclic compound selected from aminoethylpiperazine (AEP) and piperazine (PIP) and the ethanolamine-functional compound is monoethanolamine (MEA), wherein the amount of cyclic compound used in the reaction is selected such that the product comprises 50-90 wt. % straight-chain triethylenetetramine, 0-50 wt. % of cyclic triethylenetetramine, and 0-20 wt. % of branched triethylenetetramine, or the urea derivatives thereof, calculated on the total amount of triethylenetetramine in the product.

13. The process according to claim 12, wherein the amount of the starting materials are selected such that the product comprises, calculated on the total amount of triethylenetetramine present, 50-80 wt. % of straight-chain triethylenetetramine, 15-50 wt. % of cyclic triethylenetetramine, and 0-10 wt. % of branched triethylenenetetramine, or the urea derivatives thereof.

14. The process according to claim 1, wherein the reaction product comprising one or more compounds in the form of urea derivatives is subjected to a CO removal reaction to convert the urea derivatives into amine compounds.

15. The process according to claim 1, wherein the amine-functional compound comprises a non-straight-chain amine-functional compound comprising a cyclic amine-functional compound, wherein the cyclic amine-functional compound is aminoethylpiperazine, diaminoethylpiperazine, piperazinoethylpiperazine, piperazino-ethylethylenediamine, or mixtures thereof.

16. A process for manufacturing a mixture of straight-chain tetraethylenepentamine, branched tetraethylenepentamine, and cyclic tetraethylenepentamine, or urea derivatives thereof, the process comprising:
reacting a first compound with a second compound in the presence of a carbon oxide delivering agent selected from the group of carbon dioxide, urea, alkyl ureas, linear and cyclic alkylene ureas, linear and cyclic carbamates, and organic carbonates, wherein:
1) The first compound comprises a combination of diethylenetriamine (DETA) and aminoethylpiperazine (AEP) and the second compound comprises aminoethylethanolamine (AEEA);
2) The first compound comprises a combination of ethylenediamine (EDA) and aminoethylpiperazine (AEP) and the second compound comprises a combination of monoethanolamine (MEA) and aminoethylethanolamine (AEEA);
3) The first compound comprises a combination of ethylenediamine (EDA) and piperazine (PIP) and the second compound comprises a combination of monoethanolamine (MEA) and aminoethylethanolamine (AEEA);

4) The first compound comprises a combination of ethylenediamine (EDA) and piperazine (PIP) and the second compound comprises hydroxylethyldiethylenetriamine (HE-DETA); or 5) The first compound comprises a combination of one or more linear compounds selected from the group of diethylenetriamine (DETA) and triethylenetetraamine (L-TETA), and one or more non-straight-chain compounds selected from the group of branched triethylenetetraamine (T-TETA), diaminoethylpiperazine (DAEP), piperazinoethylethylenediamine (PEEDA), aminoethylpiperazine (AEP), and piperazine (PIP), and the second compound is monoethanolamine (MEA);

and wherein the relative amounts of the first compound and second compound are selected such that the mixture comprises 30-70 wt. % straight-chain tetraethylenepentamine, up to 30 wt. % branched tetraethylenepentamine, and up to 50 wt. % of cyclic tetraethylenepentamine, or urea derivatives thereof, calculated on the total amount of tetraethylenepentamine in the mixture.

17. The process according to claim 16 wherein the mixture comprises 30-70 wt. % of straight-chain tetraethylenepentamines, 15-50 wt. % of cyclic tetraethylenepentamines, and up to 30 wt. % of branched tetraethylenepentamines, or urea derivatives thereof, calculated on the total amount of tetraethylenepentamine in the mixture.

* * * * *